United States Patent [19]

Carter

[11] Patent Number: 4,911,887
[45] Date of Patent: Mar. 27, 1990

[54] PHOSPHONIC ACID COMPOUNDS AND THE PREPARATION AND USE THEREOF

[75] Inventor: Charles G. Carter, Silver Spring, Md.

[73] Assignee: W. R. Grace & Co.-Conn., New York, N.Y.

[21] Appl. No.: 269,204

[22] Filed: Nov. 9, 1988

[51] Int. Cl.$^4$ .............................. C09K 3/00; C07F 7/02
[52] U.S. Cl. .................................. 422/15; 252/389.2; 549/215; 549/346
[58] Field of Search .............................. 549/216, 346; 252/389.2, 389.23; 422/15

[56] References Cited

U.S. PATENT DOCUMENTS

| | | | |
|---|---|---|---|
| 2,535,172 | 12/1950 | Tawney | 260/461 |
| 2,632,767 | 3/1953 | Smith et al. | 260/461 |
| 2,900,408 | 8/1959 | Blaser et al. | 260/461 |
| 3,032,578 | 5/1962 | MacMullen et al. | 260/461 |
| 3,341,467 | 9/1967 | Hwa | 252/321 |
| 3,429,824 | 2/1969 | Tate | 252/180 |
| 3,488,289 | 1/1970 | Tate | 252/180 |
| 3,510,436 | 5/1970 | Silverstein et al. | 252/389 |
| 3,532,639 | 10/1970 | Hatch | 252/389 |
| 3,600,470 | 8/1971 | Lewis | 260/924 |
| 3,714,066 | 1/1973 | King et al. | 252/389 A |
| 3,738,806 | 6/1973 | Feiler | 252/389 A |
| 3,803,047 | 4/1974 | Hwa | 252/389 A |
| 3,803,048 | 4/1974 | Hwa | 252/389 A |
| 3,837,803 | 9/1974 | Carter et al. | 252/389 A |
| 3,890,228 | 6/1975 | Hwa et al. | 210/58 |
| 3,960,576 | 6/1976 | Carter et al. | 106/14 |
| 3,970,729 | 7/1976 | Walsh et al. | 260/978 |
| 4,003,842 | 1/1977 | Suen et al. | 252/175 |
| 4,029,696 | 6/1977 | Sommer et al. | 260/502.5 |
| 4,052,160 | 10/1977 | Cook et al. | 252/389 |
| 4,056,480 | 11/1977 | Herber | 252/78 |
| 4,069,247 | 1/1978 | Kleiner | 260/502.4 R |
| 4,085,134 | 4/1978 | Redmore et al. | 252/180 |
| 4,092,244 | 5/1978 | Suen et al. | 252/180 |
| 4,206,075 | 6/1980 | Boffardi | 252/180 |
| 4,209,487 | 6/1980 | Hogue et al. | 422/12 |
| 4,212,832 | 7/1980 | Mitschke et al. | 266/930 |
| 4,276,089 | 6/1981 | Moran | 252/389 |
| 4,416,830 | 11/1983 | Morr et al. | 556/405 |
| 4,440,646 | 4/1974 | Budnick | 210/699 |
| 4,465,516 | 8/1984 | Danner et al. | 252/389 |
| 4,717,542 | 1/1988 | Mitchell | 422/15 |
| 4,719,031 | 1/1988 | Coleman | 252/180 |

FOREIGN PATENT DOCUMENTS 535946 of 1957 Canada .
1076244 of 1967 United Kingdom .
2112370A of 1983 United Kingdom .

OTHER PUBLICATIONS

J. S. Amato et al., "A New Preparation of Chloromethyl Methyl Ether Free of Bis(chloromethyl) Ether", Synthesis 970–971 (1979).
T. H. Chan et al., "Unexpected Site Selectivity of Halotrimethylsilane with 2,5-Dimethoxytetrahydrofuran and 2,6-Dimethoxytetrahydropyran" Tet Lett. 24, 1225–1228 (1983).
Griffiths et al., "The Reaction of Phosphorus Trichloride and Paraformaldehyde" Phosphorous, 6, 223–230 (1976).
K. A. Petrov et al., "Synthesis and Properties of (Substituted Methyl) Phosphonates" Zhur. Obschchei. Khim. 12 2741–2749 (1977) (1978 Translation Plenum Publishing Corp., 2494–2501).
D. P. Phillion et al., "Synthesis and Reactivity of Diethyl Phosphonomethyltriflate", Tet. Lett., 27 1477–1480 (1986).
D. Redmore, "Heterocuclic Systems Bearing Phosphorus Substituents. Synthesis and Chemistry", Chem. Rev., 71, 315–337 (1971) and Table III.
L. Maier et al., "Organic Phosphorus Compounds. 70. Preparation and Properties of New Phosphorus Containing Chelating Agents for Calcium and Magnesium Ions", Phosphorous and Sulfur, 5, 45–51 (1978).
Chem. Abstracts, vol. 96, entry 183846E (1982); Stulli et al; "Effect of Complexing Agents on the Properties of Synthetic Cutting Fluids" Khim. Tekhnol. Topl. Masel.
Chem. Abstracts, vol. 95, entry 61756j (1981)—Jupe et al., "Polyhydric Phenols Ger. Offen"., 2,942,366.
D. A. Nicholson et al., "A Convenient Method of Esterification of Polyphosphonic Acids", Journal of Organic Chemistry, 35, 3149–3150 (1970).
Chemical Abstracts, vol. 37, cols. 3048–3049 (1943), V. S. Abramov et al., "Action of Dibromomethyl and Dichloromethyl Ethers on Ethyl Phosphite and Sodium Diethyl Phosphite".
Chemical Abstracts, vol. 55, col. 6367 (1961), K. A. Petrov et al., "Diphosphonates. III. Synthesis of O- and S-Diphosphonates" Zhur. Obshchei Khim. 30, 1960–1964 (1960).
Chemical Abstracts, vol. 56, cols. 11418–11419 (1962), W. Treibs et al., "Autooxidation in the Presence of Alcohols and Protons III. Autooxidation of Cyclenes, (List continued on next page.)

*Primary Examiner*—Richard L. Raymond
*Assistant Examiner*—Raymond Covington
*Attorney, Agent, or Firm*—James P. Barr

[57] ABSTRACT

The cyclic ether bis-phosphonic acids diphosphonotetrahydrofuran, diphosphonotetrahydropyran, and diphosphonooxepane and their salts and esters are disclosed, as is their use in water treatment. Also disclosed is the preparation of the cyclic ether bis-phosphonic acid compounds by reacting a corresponding dialkoxy cyclic ether with certain dialkyl phosphites, reacting the intermediate formed therefrom with certain halotrimethyl silanes, organic acid halides or inorganic acid halides, and reacting the intermediate formed therefrom with certain trialkyl phosphites to form a bis-phosphonic acid compound which may be hydrolized to form the cyclic ether bis-phosphonic acid. Certain of the first intermediates are considered stable reagents which may be used for preparing flame retardants, chelating agents and corrosion inhibitors.

22 Claims, No Drawings

OTHER PUBLICATIONS

Hydroarenes, and Hydroheterocycles" Chem. Ber. 94, 2983-2989 (1961).

Chemical Abstracts, vol. 58, cols. 6866-6868 (1963), S. Julia et al., "Synthesis of Substituted—and—Cyclohomocitrals and the Corresponding Ketones and Alcohols" Bull. Soc. Chim. Grance, 1952-1959 (1962).

Stauffer Chemical Company, Flame Retardant Chemical Product Data—Hydroxymethyl Phosphhonic Acid.

Stauffer Chemical Company, Material Safety Data Sheet, Hydroxymethylphosphonic Acid.

PHOSPHONIC ACID COMPOUNDS AND THE PREPARATION AND USE THEREOF

FIELD OF THE INVENTION

This invention relates to a novel class of phosphonic acid compounds, their preparation, and their use, and more particularly to the diphosphonocyclic ethers diphosphonotetrahydrofuran, diphosphonotetrahydropyran and diphosphonooxepane and related compounds, the preparation thereof from the corresponding dialkoxy cyclic ethers, and the use thereof in water treatment.

BACKGROUND OF THE INVENTION

Iron and iron metal containing alloys such as mild steel are well-known materials used in constructing the apparatus of aqueous systems in which system water circulates, contacts the iron based metal surface, and may be concentrated, such as by evaporation of a portion of the water from the system. Even though such metals are readily subject to corrosion in such environments, they are used over other metals due to their strength and availability.

It is known that various materials which are naturally or synthetically occurring in the aqueous systems, especially systems using water derived from natural resources such as seawater, rivers, lakes and the like, attack iron based metals (the term "iron based metals" shall mean in the present disclosure and the appended claims iron metal and metal alloys containing iron therein, i.e. ferrous metals). Typical devices in which the iron metal parts are subject to corrosion include evaporators, single and multi-pass heat exchangers, cooling towers, and associated equipment and the like. As the system water passes through or over the device, a portion of the system water evaporates causing a concentration of the dissolved materials contained in the system. These materials approach and reach a concentration at which they may cause severe pitting and corrosion which eventually requires replacement of the metal parts. Various corrosion inhibitors have been previously used.

Chromates and inorganic polyphosphates have been used in the past to inhibit the corrosion of metals which is experienced when the metals are brought into contact with water. The chromates, though effective, are highly toxic and, consequently, present handling and disposal problems The polyphosphates are relatively non-toxic, but tend to hydrolyze to form orthophosphate which in turn can create scale and sludge problems in aqueous systems. Moreover, where there is concern over eutrophication of receiving waters, excess phosphate compounds can provide disposal problems as nutrient sources Borates, nitrates, and nitrites have also been used for corrosion inhibition. These too can serve as nutrients in low concentrations, and represent potential health concerns at high concentrations. In addition, environmental considerations have also recently increased concerns over the discharge o other metals such as zinc, which previously were considered acceptable for water treatment.

Much recent research has concerned development of organic corrosion inhibitors which can reduce reliance on the traditional inorganic inhibitors. Among the organic inhibitors successfully employed are numerous organic phosphonates. These compounds may generally be used without detrimental interference from other conventional water treatment additives.

Phosphonic acid compounds have also been used in other fields for such purposes as flame retardants, plasticisers, lubricants, and surfactants. U.S. Pat. No. 3,032,578 discloses, for example, certain aryloxypolyalkylene ether phosphonates which exhibit useful properties as surface active agents, and are prepared by reacting a trialkyl phosphite with an aryloxypolyalkylene ether halide to form the corresponding dialkyl phosphonate, which is hydrolyzed to the corresponding phosphonic acid.

SUMMARY OF THE INVENTION

This invention relates to a novel class of cyclic ether bis-phosphonic acid compounds, and certain of their precursors. We have found that certain cyclic ether bis-phosphonic acid compounds may be prepared by a method which comprises the steps of (a) reacting a compound selected from the group consisting of 2,5-dialkoxytetrahydrofuran, 2,6-dialkoxytetrahydropyran and 2,7-dialkoxyoxepane (the alkoxy groups having from 1 to 4 carbon atoms) with a dialkyl phosphite having the formula $HPO(OR')_2$ wherein $R'$ is selected from the group consisting of alkyl groups having from one to eight carbon atoms to form a first intermediate; (b) reacting said first intermediate with a compound selected from the group consisting of bromotrimethyl silane, iodotrimethyl silane, organic acid halides such as phosgene, oxallyl chloride, acetyl chloride and acetyl bromide and inorganic acid halides such as $PCl_3$ and $SOCl_2$ to form a second intermediate; and (c) reacting said second intermediate with a trialkyl phosphite having the formula $P(OR'')_3$ wherein $R''$ is selected from the group consisting of alkyl groups having from one to eight carbon atoms to form a third intermediate. The reaction product of step (c) may be hydrolyzed to form a cyclic ether bis-phosphonic acid. The novel cyclic ether bis-phosphonic acid compounds 2,5-diphosphonotetrahydrofuran, 2,6-diphosphonotetrahydropyran and 2,7-diphosphonooxepane, their water soluble salts, and their esters with alkyl groups having 1 to 20 carbon atoms are provided in accordance with this invention. Certain precursors of these bis-phosphonic acid compounds are also provided in accordance with this invention, especially those corresponding to the first intermediate as described above. In another aspect of this invention, a process for inhibiting corrosion of an iron based metal in contact with the system water in an aqueous system is provided, which comprises incorporating into the system water an effective amount of a compound selected from the cyclic ether bis-phosphonic acids and their water soluble salts.

It is an object of this invention to provide new and useful phosphonic acid compounds.

It is another object of this invention to provide a novel method of preparing new and useful phosphonic acid compounds.

It is still another object of this invention to provide a novel process for inhibiting the corrosion of iron-based metal in aqueous systems.

These and other objects of this invention will become apparent from the detailed description which follows.

DETAILED DESCRIPTION

This invention relates to novel bis-phosphonic acid compounds having the general formula

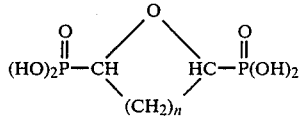

wherein n is an integer from 2 to 4, water soluble salts thereof, and esters thereof with alkyl groups having from 1 to 20 carbons. A preferred group of these compounds for water treatment includes 2,5-diphosphonotetrahydrofuran ("DPTHF"), 2,6-diphosphonotetrahydropyran ("DPTHP") and 2,7-diphosphonooxepane ("DPO") and their water soluble salts. Alkali meta salts of 2,5-diphosphonotetrahydrofuran are considered particularly useful for corrosion control applications.

The cyclic ether bis-phosphonic acids of this invention can be prepared using a process comprising the steps of (a) reacting a compound selected from the group of compounds having the formula

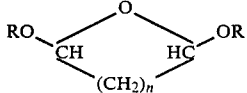

wherein each R is selected from the group consisting of alkyl groups having from 1 to 4 carbon atoms, and n is 2, 3, or 4, with a dialkyl phosphite having the formula $HPO(OR')_2$ wherein R' is selected from the group consisting of alkyl groups having from 1 to 8 carbon atoms to form a first intermediate; (b) reacting said first intermediate with bromotrimethyl silane or iodotrimethyl silane to form a second intermediate; and (c) reacting said second intermediate with a trialkyl phosphite having the formula $P(OR'')_3$ wherein R'' is selected from the group consisting of alkyl groups having from 1 to 8 carbon atoms to form a third intermediate. The third intermediate of step (c) may then be hydrolyzed to yield the bis-phosphonic acids having the formula

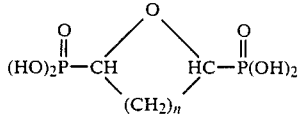

wherein n is as recited above.

To make 2,5-diphosphonotetrahydrofuran (i.e. n is 2), step (a) is suitably accomplished by adding dimethyl phosphite to a cool slurry of sodium hydride in 2,5-dimethoxytetrahydrofuran under an inert atmosphere such as nitrogen or argon and heating the resulting reaction mixture to form 2-phosphono-5-methoxytetrahydrofuran as a first intermediate. Step (b) is suitably accomplished by adding bromotrimethyl silane to said first intermediate and stirring the resulting mixture under an inert atmosphere such as nitrogen or argon, thereby forming di-(trimethylsilyl)2-phosphono-5-bromotetrahydrofuran as a second intermediate. Step (c) is suitably accomplished by adding triisopropyl phosphite to said second intermediate and heating the mixture under an inert atmosphere such as nitrogen or argon, thereby forming 2-(di-(trimethyl silyl)phosphono)-5-(diisopropylphosphono)-tetrahydrofuran. Diphosphonotetrahydrofuran may be produced by adding a concentrated acid, such as hydrochloric acid to the 2-(di-(trimethyl silyl)phosphono)-5-(diisopropylphosphono)-tetrahydrofuran and refluxing the acid solution. 2,6-Diphosphonotetrahydropyran (i.e. n is 3) and 2,7-Diphosphonooxepane (i.e. n is 4) may be produced in similar fashion, respectively using 2,6-dimethoxytetrahydropyran and 2,7-dimethoxyoxepane rather than 2,5-dimethoxytetrahydrofuran as a starting material.

The sodium hydride catalyst of step (a) may be replaced by another basic catalyst such as other alkali metal hydrides, alkali metal hydroxides, or alkali metal alkoxides; or alternatively by an acid catalyst as paratoluenesulfonic acid.

We prefer to remove the more volatile impurities produced in step (a) by vacuum and to distill the remaining residue to further purify the first intermediate before proceeding to step (b). The first intermediate as described above comprises a compound corresponding to the formula

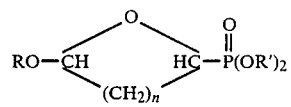

These first intermediates are considered stable reagents which are useful for preparing flame retardants, chelating agents, and as disclosed herein, corrosion inhibitors.

We prefer to remove the more volatile impurities produced in step (b) under vacuum before proceeding to step (c). The second intermediate derived from halotrimethyl silane as described above comprises a compound corresponding to the formula

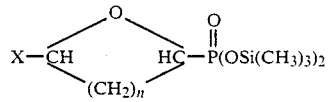

wherein X is Br or I; and the corresponding third intermediate as described above comprises a compound represented by the formula

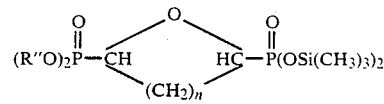

The third intermediates derived from halotrimethyl silane and trialkyl phosphite, and having this formula are considered useful as intermediates in the preparation of chelating agents and corrosion inhibitors.

The halotrimethyl silane used in step (b) above can be replaced with an organic acid halide (for example, phosgene, oxallyl chloride, acetyl chloride and acetyl bromide) or an inorganic acid halide (for example $PCl_3$ and $SOCl_2$). This may result, of course in production of alternative second intermediates and third intermediates. In one particularly useful embodiment, for example, where an inorganic acid chloride, an inorganic acid bromide, an organic acid bromide (e.g. acetyl bromide) or an organic acid chloride (e.g. acetyl chloride) is used, rather than the halotrimethyl silane, the second intermediate comprises a compound represented by the formula

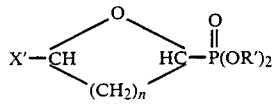

wherein R' is an alkyl group having from 1 to 8 carbon atoms and X' is Cl or Br; and the corresponding third intermediate comprises a compound represented by the formula

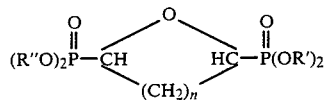

The third intermediates derived from acetyl halide and trialkylphosphite and having this formula are considered useful as flame retardants.

In any case, whether derived from halotrimethyl silane or not, the esters produced by step (c) represent useful compounds which may be hydrolyzed to produce the corresponding cyclic ether bis-phosphonic acid and water soluble salts thereof, which are corrosion inhibiting agents. The more volatile impurities produced during step (c) and the subsequent hydrolysis of the esters of the cyclic ether bis-phosphonic acids may be separated from the cyclic ether bis-phosphonic acid by vacuum.

The 2,5-dimethoxytetrahydrofuran, which may be used in step (a) can be obtained from commercial sources. The 2,6-dimethoxytetrahydropyran and 2,7-dimethoxyoxepane which may be used in step (a) may be respectively prepared in accordance with the procedures provided in S. Julia et al., *Bull Soc. Chim. France*, 1952-1959 (1962) and W. Treibs et al., *Chem. Ber.*, 94, 2983-2989 (1961).

The dimethylphosphite which may be used in step (a), the bromotrimethyl silane which may be used in step (b), the acetyl chloride which may be used in step (b), and the triisopropyl phosphite which may be used in step (c) are all readily available from commercial sources such as Aldrich Chemicals, Milwaukee, Wisc.

Salts of the cyclic ether bis-phosphonic acids of this invention may be straightforwardly produced by neutralizing the acid with the appropriate base. While esters may be produced as described above, they may also be prepared from the cyclic ether bis-phosphonic acid through conventional phosphonic acid esterification techniques (See, for example, D. A. Nicholson et al., Journal of Organic Chemistry, 35, 3149 (1970)).

2,5-Diphosphonotetrahydrofuran, 2,6-diphosphonotetrahydropyran and 2,7-diphosphonooxepane and their water soluble salts are considered useful as corrosion control agents for inhibiting the corrosion of iron based metals which are in contact with the system water in aqueous systems such as cooling water systems. The cyclic ether bis-phosphonic acids and their alkali metal salts are preferred for this purpose. Accordingly, corrosion may be inhibited by incorporating an effective amount of these materials into the system water The precise dosage of the cyclic ether bis-phosphonic acid or salt thereof depends, to some extent, on the nature of the aqueous system in which it is to be incorporated and the degree of protection desired. In general, however, it can be said the concentration maintained in the system water can be from about 0.5 to about 10,000 ppm. Within this range, generally low dosages of from about 1 to about 100 ppm are normally sufficient, and even a comparatively low dosage of from about 1 to about 50 ppm substantially inhibits corrosion in aqueous systems such as cooling water systems. The exact amount required with respect to a particular aqueous system can be readily determined in conventional manners.

The cyclic ether bis-phosphonic acid or salt thereof may be added to the system water coming in contact with the metal surfaces of an apparatus by any convenient mode, such as by first forming a concentrated solution of the cyclic ether bis-phosphonic acid or salt with water (preferably containing between 1 and 50 total weight percent of the cyclic ether bis-phosphonic acid or salt) and then feeding the concentrated solution to the system water at some convenient point in the system.

The corrosion inhibition achieved by this invention is particularly suited for cooling water systems and the like in which the system water is substantially free of chromate. The corrosion inhibiting cyclic ether bis-phosphonic acids and their salts can be used effectively without the presence of any or all of polyphosphate, nitrate, nitrite, borate or other ferrous metal corrosion inhibitors such as zinc. The combination will also function without phosphate and thus should reduce reliance upon phosphate as a corrosion inibiting agent as well However, it should be anticipated that the cyclic ether bis-phosphonic acid and salts of this invention may, like many phosphonates, eventually degrade, releasing phosphate at a rate dependent upon the conditions and chemistry of the system.

The cyclic ether bis-phosphonic acids of this invention and their alkali metal salts are considered especially useful as corrosion inhibitors in system waters having calcium hardness of at least about 75 ppm (as $CaCO_3$). Without limiting this aspect of the invention to a particular theory of operation, it is believed that the structure of the compounds and in particular the position of the phosphonate groups in relation to the cyclic ether oxygen, are advantageously suited for interaction with divalent and trivalent cations to form complexes.

Practice of the invention will become further apparent from the following non-limiting examples.

EXAMPLE I

Sodium hydride (0.12 g, 5.0 mmol) was slurried in 2,5-dimethoxytetrahydrofuran (6.8 ml, 50 mmol) under a nitrogen atmosphere and cooled with an ice bath. Dimethyl phosphite (4.6 ml, 60 mmol) was then added dropwise over a 30 minute period. The ice bath was then removed and the reaction mixture was heated to 100° C. for one hour. After standing overnight at room temperature, the mixture was heated to reflux (i.e. about 125° C.) for four hours. At this point another 40 mg (1.7 mmol) of sodium hydride was added and the reflux was continued for another three hours. The mixture was then allowed to stand overnight (i.e. about 16 hours) at room temperature again The reaction was then heated at reflux for another three and one half hours during which an additional 1.0 ml (10 mmol) of dimethyl phosphite was added in two portions. After removal of more volatile impurities under vacuum the residue was distilled to yield 5.1 g of a liquid. This was identified as dimethyl 2-phosphono-5-methoxytetrahydrofuran contaminated with a small amount (i.e. about 7%) of dimethyl 5-phosphono-4,5-dihydrofuran by gas chromatography, proton nuclear magnetic resonance spectroscopy and mass spectroscopy.

EXAMPLE II

Bromotrimethyl silane (0.51 ml, 3.8 mmol) was added to dimethyl 2-phosphono-5-methoxytetrahydrofuran prepared in accordance with the process of Example I and the mixture was heated under a nitrogen atmosphere with a 75° C. oil bath for three hours. The volatile components were then removed under vacuum to give di-(trimethylsilyl) 2-phosphono-5-bromotetrahydrofuran. The structure of the product was confirmed by proton nuclear magnetic resonance spectroscopy.

EXAMPLE III

Triisopropyl phosphite (0.33 ml, 1.2 mmol) was added to the 2-phosphono-5-bromotetrahydrofuran prepared in accordance with the process of Example II. The mixture was heated over a period of one half hour under a nitrogen atmosphere to 170° C. It was held at this temperature for two and one quarter hours and then cooled to room temperature. Concentrated hydrochloric acid (15 ml) was added and the resulting mixture was heated to reflux for five hours. The volatile components were removed under vacuum leaving 2,5-diphosphonotetrahydrofuran ("DPTHF") containing phosphorous acid as an impurity. The identity of the 2,5-diphosphonotetrahydrofuran was established by nuclear magnetic resonance spectroscopy (proton, phosphorus and carbon-13) and fast atom bombardment mass spectroscopy

EXAMPLE IV

Dimethyl 2-phosphono-5-methoxytetrahydrofuran (1.2 g, 5.7 mmol) prepared in accordance with the process of Example I was placed in a flask under a nitrogen atmosphere. Acetyl chloride (0.66 g, 8.4 mmol) was added and the resulting mixture was stirred at room temperature for 30 hours. Examination of an aliquot of the resulting product by proton nuclear magnetic resonance spectroscopy showed about 80% conversion of the dimethyl 2-phosphono-5-methoxytetrahydrofuran to dimethyl 2-phosphone-5-chlorotetrahydrofuran.

EXAMPLE V 1.1 g (14 mmol) of acetyl chloride was added to 1.3 g (5 mmol) of crude dimethyl 2-phosphono-5-methoxytetrahydrofuran (about 80% pure) prepared in accordance with the process of Example I. The mixture was stirred for 6 hours under a nitrogen atmosphere. Examination of the resulting dimethyl 2-phosphono-5-chlorotetrahydrofuran showed that only a trace of 2-phosphono-5-methoxytetrahydrofuran remained.

EXAMPLE VI

Triisopropyl phosphite (1.8 g, 8.5 mmol) was added to the dimethyl 2-phosphono-5-chlorotetrahydrofuran prepared in accordance with the process of Example V, and the mixture was stirred at room temperature under a nitrogen atmosphere for 64 hours. The mixture was subsequently heated for 4 hours using a 150° C. oil bath, and then respectively cooled, diluted with diethyl ether, washed with saturated sodium bicarbonate, dried over anhydrous sodium sulfate, filtered, and concentrated under vaccum. Volatile impurities were removed from the resulting brown liquid (1.7 g) by bulb-to-bulb distillation under vacuum, to yield a residue (1.1 g) of a viscous oil. The oil was identified as tetraisopropyl 2,5-diphosphonotetrahydrofuran by a combination of proton, carbon and phosphorous nuclear magnetic resonance spectroscopy, and gas chromotography coupled with mass spectrometry.

EXAMPLE VII

A standard corrosive test water solution containing 30 milligrams per liter (mg/l) calcium chloride, 37 mg/l magnesium sulfate, 100 mg/l sodium sulfate, 50 mg/l sodium chloride, and 100 mg/l sodium carbonate was prepared by adding the recited salts to distilled water. The test solution was thus free of such materials as chromate, zinc, phosphate, polyphosphate, nitrite, nitrate and borate. 850 milliliters of the standard corrosive test water was added to an aerated solution bottle which was situated in a bath thermostatically held at 55° C. The temperature of the standard corrosive test water solution was allowed to equilibrate and the pH was adjusted to about 8.5 using either aqueous sodium hydroxide or sulfuric acid as appropriate. Two mild steel coupons (4.5 inches by 0.5 inches) which had been cleaned (by immersing them in 15% hydrochloric acid for 15 minutes and then rinsing them sequentially in saturated sodium bicarbonate solution, distilled water and isopropanol), dried, stored in a dessicator, and weighed were then immersed in the standard corrosive test water, and air was passed through the solution at about 250 milliliters per minute. After 48 hours, the coupons were removed, cleaned with steel wool, rinsed, dried and reweighed. The rate of corrosion was calculated from the weight loss of the coupons to be 68.9 mils per year. A second run was made using the same procedure except that 150 parts per million (ppm) of 2,5-diphosphonotetrahydrofuran, prepared generally in accordance with the procedure illustrated above in Examples I through VI, was added to the standard corrosive test water solution. The corrosion rate of the coupons in the second run was found to be reduced by about 54% when compared to the rate observed with the standard corrosive test water solution alone.

EXAMPLE VIII

A second standard corrosive test water solution containing 12.8 mg/l calcium chloride, 110.7 mg/l calcium sulfate dihydrate, 54.6 mg/l magnesium sulfate, and 175.7 mg/l sodium bicarbonate was prepared by adding the recited salts to distilled water. The second test solution was thus free of such materials as chromite, zinc, phosphate, polyphosphate, nitrite, nitrate and borate. 850 milliliters of the second standard corrosive test water was added to an aerated solution bottle which was situated in a bath thermostatically held at 55° C. The temperature of the second standard corrosive test water solution was allowed to equilibrate and the pH was adjusted to about 8.5 using NaOH or $H_2SO_4$ as appropriate. Two mild steel coupons which had been cleaned dried and stored as in Example VII were weighed and immersed in the second standard corrosive test water and air was passed through the solution at about 250 milliliters per minute. After 48 hours, the coupons were removed, cleaned with steel wool, rinsed, dried and reweighed. The rate of corrosion was calculated from the weight loss of the coupons to be 57.7 mils per year. Three other runs were made using the same procedure except that 50 ppm, 75 ppm and 100 ppm of 2,5-diphosphonotetrahydrofuran, prepared generally in accordance with the procedure illustrated above, were respectively added to the second standard corrosive test water solution. The corrosion rate using 50 ppm of the diphosphonotetrahydrofuran was found to be reduced by about 54%, the corrosion rate using 75 ppm of the diphosphonotetrahydrofuran was found to be reduced by about 81%, and the corrosion rate using 100 ppm of the diphosphonotetrahydrofuran was found to be reduced by about 90%, all compared to the rate observed with the second corrosive test water solution alone.

EXAMPLE IX

A third standard corrosive test water solution containing 25.6 mg/l calcium chloride, 221.4 mg/l calcium sulfate dihydrate, 109.2 mg/l magnesium sulfate and 351.4 mg/l sodium bicarbonate was prepared by adding the recited salts to distilled water. The third solution was thus free from such materials as chromate, zinc, phosphate polyphosphate, nitrite, nitrate and borate. 850 milliliters of the third standard corrosive test water was added to an aerated solution bottle which was situated in a bath thermostatically held at 55° C. The temperature of the third standard corrosive test water solution was allowed to equilibrate and the pH was adjusted to about 8.5 using NaOH or $H_2SO_4$ as appropriate. Two mild steel coupons which had been cleaned, dried, and stored as in Example VII were weighed and immersed in the mild standard corrosive test water and air was passed through the solution at about 250 milliliters per minute. After 48 hours, the coupons were removed, cleaned with steel wool, rinsed, dried and reweighed. The rate of corrosion was calculated from the weight loss of the coupons to be 57.9 mils per year. A second run was made using the same procedure except that 50 ppm of 2,5-diphosphonotetrahydrafuron, prepared generally in accordance with the procedure illustrated above, was added to the third standard corrosive test water solution. The corrosion rate of the coupons in the second run was found to be reduced by about 89% when compared to the rate observed with the third standard corrosion test water solution alone.

It will be appreciated that while the cyclic ether bis-phosphonic acid or salt thereof of this invention may be used as the sole corrosion inhibitor for an aqueous system, other ingredients customarily employed in aqueous systems of the type treated herein can be used in addition to the subject compounds. Such water treatment additives are, for example, biocides, lignin derivatives, polymeric agents (e.g. copolymers of 2-acrylamido-2-methylpropane sulfonic acid and methacrylic acid), yellow metal corrosion inhibitors (e.g. benzotriazlle), and the like. Of particular note are combinations of the cyclic ether bis-phosphonic acids and water-soluble salts of this invention with phosphonates such as hydroxymethyl phosphonic acid, 1-hydroxyethylidene-1,1-diphosphonic acid, hydroxyphosphonoacetic acid, 2-phosphonobutane-1,2,4-tricarboxylic acid and their water soluble salts. Advantageous combinations with zinc and phosphate may also be used.

The Examples describe particular embodiments of the invention. Other embodiments will become apparent to those skilled in the art from a consideration of the specification or practice of the invention disclosed herein. It is understood that modifications and variations may be produced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A compound of the formula

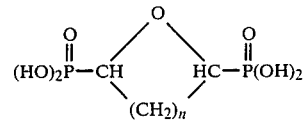

wherein n is an integer from 2 to 4, water soluble salts thereof, and esters thereof with alkyl groups having 1 to 20 carbon atoms.

2. A compound according to claim 1 wherein the compound is selected from the group consisting of 2,5-diphosphonotetrahydrofuran, 2,6-diphosphonotetrahydropyran, and 2,7-diphosphonooxepane and their water soluble salts.

3. A compound according to claim 1 wherein n is 2.

4. A compound according to claim 3 wherein the compound is selected from the tetraalkyl esters of 2,5-diphosphonotetrahydrofuran.

5. A compound according to claim 3 wherein the compound is selected from 2,5-diphosphonotetrahydrofuran and its alkali metal salts.

6. A compound according to claim 1 wherein n is 3.

7. A compound according to claim 6 wherein the compound is selected from the tetraalkyl esters of 2,6-diphosphonotetrahydropyran.

8. A compound according to claim 6 wherein the compound is selected from 2,6-diphosphonotetrahydropyran and its alkali metal salts.

9. A compound according to claim 1 wherein n is 4.

10. A compound according to claim 9 wherein the compound is selected from the tetraalkyl esters of 2,7-diphosphonooxepane.

11. A compound according to claim 9 wherein the compound is selected from 2,7-diphosphonooxepane and its alkali metal salts.

12. A method of preparing a cyclic ether bis-phosphonic acid compound comprising the steps of: (a) reacting a compound selected from the group of compounds having the formula

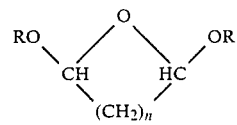

wherein each R is selected from the group consisting of alkyl groups having from 1 to 4 carbon atoms, and n is 2, 3 or 4, with a dialkyl phosphite having the formula HPO(OR')$_2$ wherein R' is selected from the group consisting of alkyl groups having from 1 to 8 carbon atoms to form a first intermediate;

(b) reacting said first intermediate with a compound selected from the group consisting of bromotrimethyl silane, iodotrimethyl silane, organic acid halides and inorganic acid halides to form a second intermediate; and (c) reacting said second intermediate with a trialkyl phosphite having the formula P(OR'')$_3$ wherein R'' is selected from the group consisting of alkyl groups having from 1 to 8 carbon atoms to form a third intermediate.

13. The method of claim 12 further comprising the step of hydrolyzing the third intermediate to form a cyclic ether bis-phosphonic acid.

14. The method of claim 12 wherein, in step (a) 2,5-dimethoxytetrahydrofuran is reacted with dimethyl phosphite; wherein, in step (b), bromotrimethyl silane or iodotrimethyl silane is reacted with said first intermediate; and wherein, in step (c) triisopropyl phosphite is reacted with said second intermediate; and wherein said third intermediate is hydrolyzed to produce 2,5-diphosphonotetrahydrofuran.

15. The method of claim 12 wherein in step (b), said first intermediate is reacted with acetyl chloride or acetyl bromide; and wherein said third intermediate is a cyclic ether bis-phosphonic acid compound having the formula

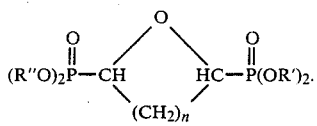

16. The method of claim 12 wherein in step (b) said first intermediate is reacted with phosgene, oxallyl chloride, acetyl chloride, acetyl bromide, phosphorous trichloride or thionyl chloride.

17. A process for inhibiting corrosion of an iron based metal in contact with the system water in an aqueous system comprising incorporating into the system water an effective amount of a cyclic ether bis-phosphonic acid compound selected from the group consisting of 2,5-diphosphonotetrahydrofuran, 2,6-diphosphonotetrahydropyran, and 2,7-diphosphonooxepane and their water soluble salts.

18. A process according to claim 17 wherein a concentration of from about 0.5 to about 10,000 ppm of 2,5-diphosphonotetrahydrofuran is maintained in the system water.

19. A process according to claim 17 wherein the system water has a calcium hardness of at least about 75 ppm.

20. A process according to claim 19 wherein a concentration from about 0.5 to about 10,000 ppm of 2,5-diphosphonotetrahydrofuran is maintained in the system water.

21. A process according to claim 17 wherein the aqueous system is a cooling water system.

22. A compound of the formula

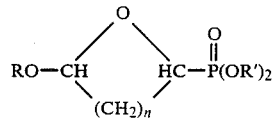

wherein R is selected from the group consisting of alkyl groups having from 1 to 4 carbon atoms, wherein R' is selected from the group consisting of alkyl groups having from 1 to 8 carbon atoms, and wherein n is 2, 3 or 4.

* * * * *